US007934435B2

(12) United States Patent
Brackley et al.

(10) Patent No.: US 7,934,435 B2
(45) Date of Patent: May 3, 2011

(54) MODULAR GLASS REFERENCE PLATE ASSEMBLY

(75) Inventors: Douglas E Brackley, Horseheads, NY (US); Kiat Chyai Kang, Taichung (TW); Paul Maynard Schermerhorn, Painted Post, NY (US); Mark Alex Shalkey, Corning, NY (US); Paul John Shustack, Elmira, NY (US)

(73) Assignee: Corning Incorporated, Corning, NY (US)

( * ) Notice: Subject to any disclaimer, the term of this patent is extended or adjusted under 35 U.S.C. 154(b) by 1167 days.

(21) Appl. No.: 11/634,598

(22) Filed: Dec. 6, 2006

(65) Prior Publication Data

US 2008/0138559 A1    Jun. 12, 2008

(51) Int. Cl.
*G01N 33/00* (2006.01)
*B32B 17/00* (2006.01)

(52) U.S. Cl. .......................................... 73/866; 156/99
(58) Field of Classification Search .................... 73/866; 156/99, 292, 297, 298, 305
See application file for complete search history.

(56) References Cited

U.S. PATENT DOCUMENTS

| | | | | |
|---|---|---|---|---|
| 2,858,582 A * | 11/1958 | Toulmin, Jr. | ................. | 52/578 |
| 4,610,901 A * | 9/1986 | Linscott | ..................... | 428/38 |
| 4,730,429 A * | 3/1988 | Roberts | .................... | 52/309.13 |
| 5,499,451 A * | 3/1996 | Krivda et al. | ............... | 29/897.2 |
| 5,558,827 A * | 9/1996 | Howes | ........................ | 264/220 |
| 5,661,531 A | 8/1997 | Greene et al. | .................. | 349/73 |
| 5,903,328 A | 5/1999 | Greene et al. | .................. | 349/73 |
| 6,556,261 B1 | 4/2003 | Krusius et al. | ................. | 349/73 |
| 6,650,393 B1 * | 11/2003 | Nishiguchi | .................. | 349/156 |
| 6,661,481 B2 | 12/2003 | Suzuki | ........................ | 349/73 |
| 6,813,904 B2 | 11/2004 | Elledge | ....................... | 65/102 |
| 7,145,611 B2 | 12/2006 | Dubin et al. | ..................... | 349/5 |
| 2001/0028420 A1 * | 10/2001 | Suzuki | ........................ | 349/73 |
| 2002/0048438 A1 * | 4/2002 | Veligdan | ..................... | 385/120 |
| 2003/0101562 A1 * | 6/2003 | Hanna et al. | ................... | 29/412 |
| 2008/0110205 A1 * | 5/2008 | Adriaansen et al. | .......... | 65/29.12 |

* cited by examiner

*Primary Examiner* — Hezron Williams
*Assistant Examiner* — Tamiko D Bellamy
(74) *Attorney, Agent, or Firm* — Thomas R. Beall

(57) ABSTRACT

Systems, methods, and apparatus relate to a glass reference plate panel; to a modular glass reference plate assembly; and to creation of the modular glass reference plate assembly, which may include providing a plurality of glass reference plate panels, arranging the plurality of glass reference plate panels into an array of adjoining glass reference plate panels, and adhering together the adjoining glass reference plate panels. One or more embodiments may include 6.8 mm-thick borosilicate glass, ground, and polished, with reference marks on a top side and a PVD aluminum coating on a bottom side, perforated with holes, arranged in a 4×4 array of 16 glass reference plate panels, each approximately 810 mm$^2$ in size, abutting at interfaces formed by lap joints, and bonded together with a UV-curable adhesive into a contiguous piece.

28 Claims, 7 Drawing Sheets

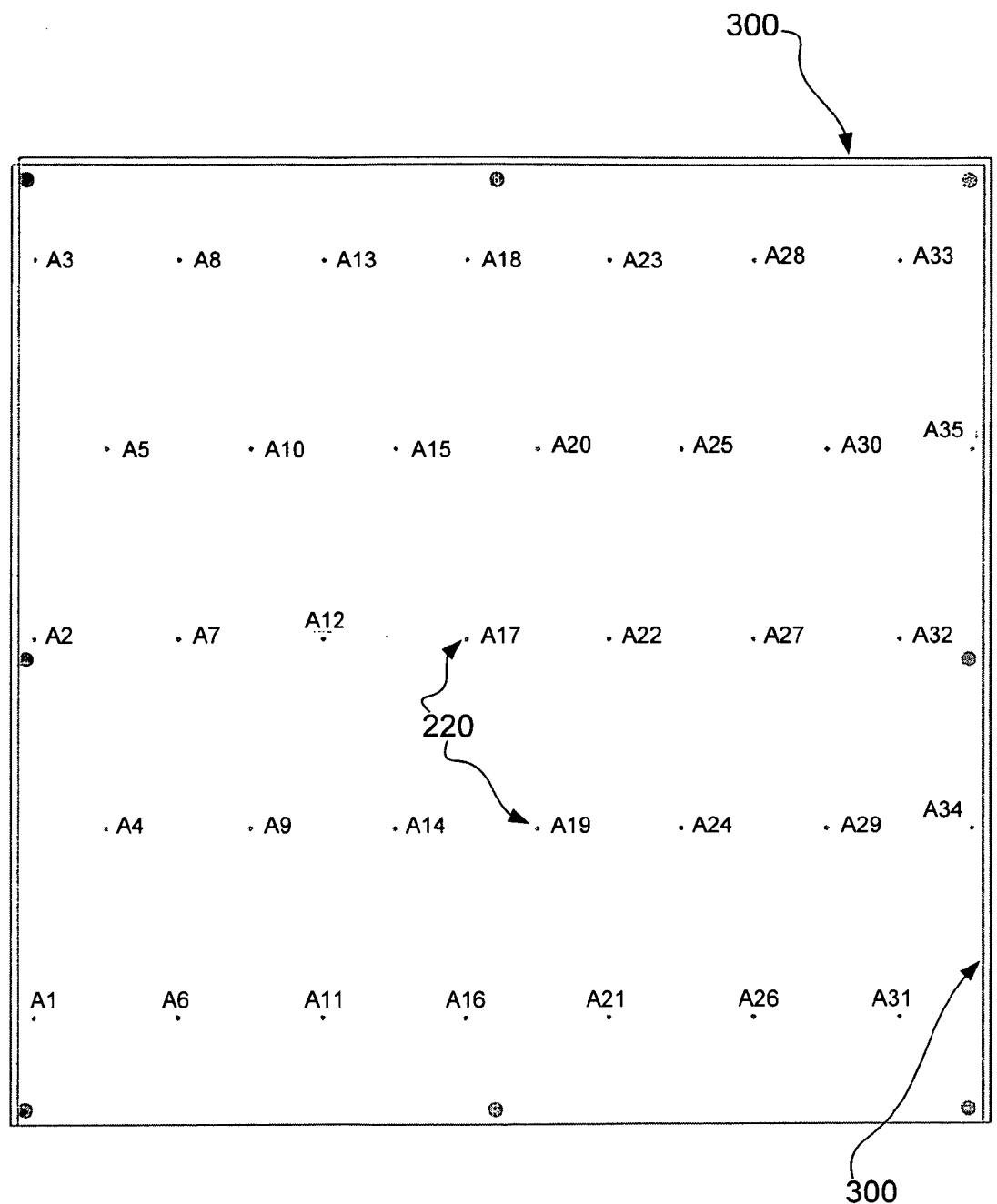

400

400

400

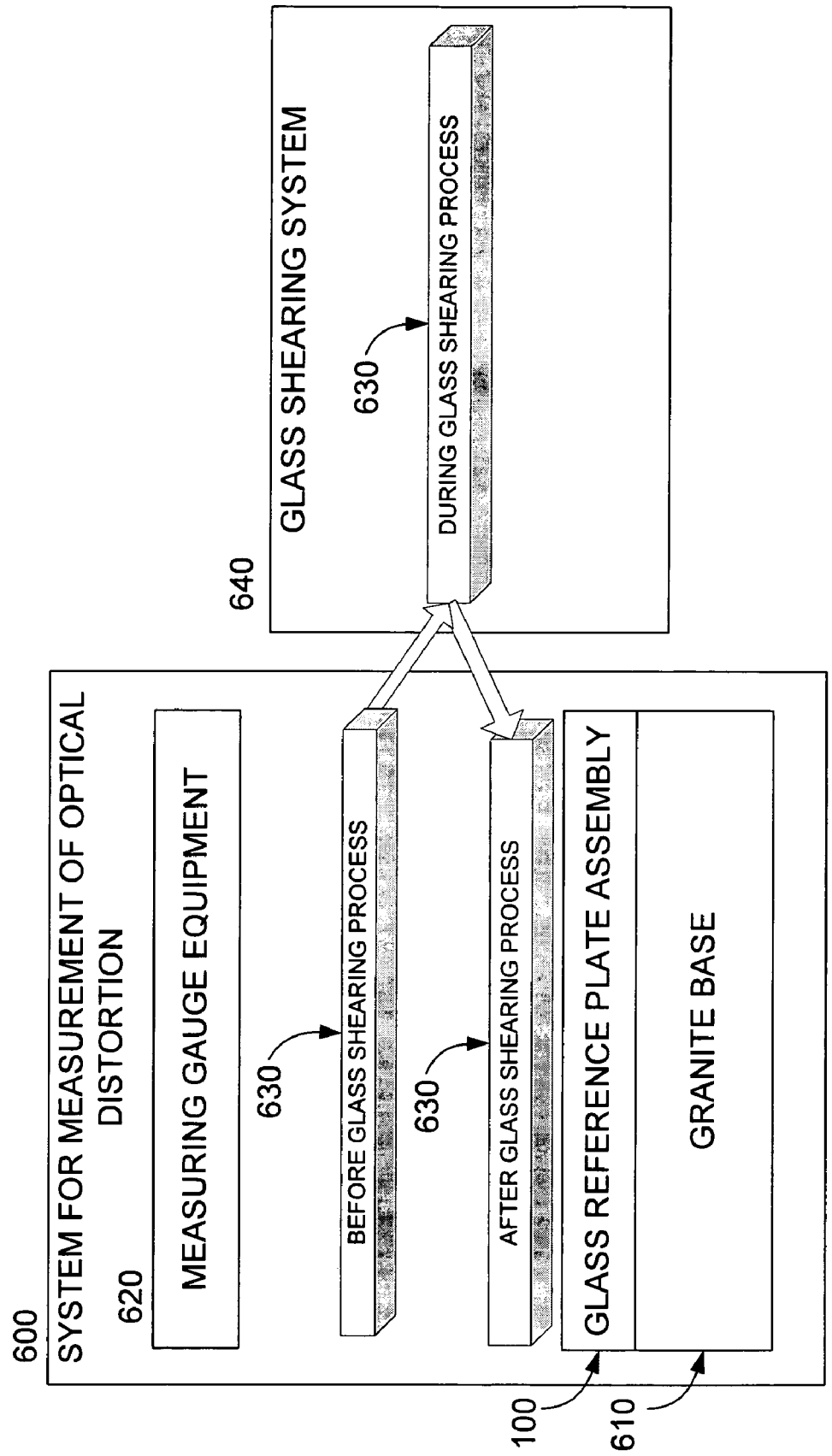

MODULAR GLASS REFERENCE PLATE ASSEMBLY

BACKGROUND

1. Field of Invention

The present invention relates to methods and apparatus relating to a precision scribed glass master, and in particular to a modular glass reference plate assembly, which may include an array of glass reference plate panels adhered together.

2. Description of Related Art

Producing flat product glass for the display business involves many challenges. A key requirement in this process is the ability to measure product distortion due to internal stresses in large product glass plates. Typical large product glass plates range in size up to 3.2 meters square. Optical methods and gauging techniques have developed over the past several years to enable distortion measurement via optical means. Distortion measurements may be performed by comparing scribed reference marks on the product glass with scribed reference marks on a precision scribed glass master, before and after the glass shearing process. A measured difference between such scribe marks is indicative of a level of stress in the product glass.

One such measurement apparatus is a distortion gauge, which is able to measure display glass up to 3.2 meters square. Among its various parts, a distortion gauge includes a granite base, a precision scribed glass master on top of the granite base, and optical measurement equipment. In the past, a glass master comprised of a single sheet of glass was used because of small glass product sizes that were being measured. To accommodate the desire for larger product glass sizes, use of a single sheet glass master was attempted for the 3.2 meters square sizes. However, reference glass of this size presently is difficult to create and not advantageous. Even minor damage to a portion of the reference glass may require replacement of the entire single sheet. Nevertheless, it would be desirable to have a suitable glass master able to handle larger glass product sizes.

It would therefore be desirable to further scale up the quality controls applicable to the manufacture of larger product glass sheets by creating larger precision scribed glass masters, while minimizing the challenges and risks associated with such large glass reference plates.

SUMMARY OF THE INVENTION

In accordance with one or more embodiments of the present invention, systems, methods and apparatus relate to a modular glass reference plate panel, to a modular glass reference plate assembly, and to creation of the modular glass reference plate assembly, which may include providing a plurality of glass reference plate panels, arranging the plurality of glass reference plate panels into an array of adjoining glass reference plate panels, and adhering together the adjoining glass reference plate panels.

According to one or more embodiments of the present invention, the glass reference plate panels are made using a glass having a coefficient of thermal expansion (CTE) similar to those of the product glass to be measured. One or more embodiments of the glass reference plate may be constructed of Schott Borofloat Borosilicate Glass, ground and polished on both sides for a finished thickness of 6.8 mm. The top side of the plate may be scribed for use as measurement witness marks. The bottom side of the plate may have an opaque and/or reflective coating, such as a thin layer of PVD aluminum protected by glass. Each plate may be perforated with holes to allow fluid flow (e.g., a liquid or gas, such as air) as necessary to float (via positive pressure) or hold (via negative pressure or suction) the product glass as required.

According to one or more embodiments of the present invention, the glass reference plate assembly may be built using 16 reference plate panels, each approximtely 810 square mm in size, arranged in a 4×4 array, and bonded together into a contiguous piece. The plate panels may be bonded with an adhesive having properties matched to the glass, such as a UV-curable adhesive. One or more embodiments may use a UV-curable adhesive coded BPA-3 from Corning Incorporated. The UV-curable adhesive may be applied with a specially designed adhesive applicator with a commercial dispensing system and cured with a UV lamp of appropriate wavelength emission.

According to one or more embodiments of the present invention, each glass reference plate panel may include a lap joint on the edges to facilitate even and stable interfaces with the edges of the adjoining plate panels. Each plate panel of may abut with each adjoining plate panel via reference surfaces on the edge planes of the individual plate panels. Inasmuch as each plate panel is well machined to thickness, further finishing may be avoided following assembly.

The advantages of this invention are best understood after reading the detailed technical description, and in relation to existing glass quality control processes. Nonetheless, the advantages may include the scalability of the process and system to large product glass and correspondingly large reference plates. As the product glass sheets increase in size, the size of the array may be increased by adding plate panels, by enlarging the plate panels themselves, or both. Larger reference plates facilitate quality control of the manufacture of larger glass products. This scalability potentially extends the product life of the glass master and distortion gauge, as customer substrate size requirements increase or change.

Among other advantages, the modular design and smaller component size may allow for plate panel manufacture with high precision and refined surface finishes required by the measurement operation of the finished gauge. Modular assembly may also allow replacement and reassembly in the event of error or breakage of a plate panel. Moreover, the modular design may offer the ability within a single assembly to apply and try different opaque and/or reflective coatings on the backside of various plate panels against the granite surface.

At 22 pounds per plate panel, individual plate panels may be light and easy to handle, with a robust 6.8 mm finish thickness. The smaller plate panel size allows plate panels to be manufactured with well-known and proven conventional machining, polish finishing and metrology methods. Risk management during fabrication of the panels is simplified and diversified, as risk is divided over a quantity of smaller component parts and a couple of routine procedures. Variation of the glass reference plate structure is possible, as the parameters (size, shape, thickness, composition, etc.) of the plate panels and plate array are varied with less difficulty and expense.

Use of UV-curable adhesive in construction allows disassembly and reassembly in the event of issues regarding alignment or initial assembly prior to curing the adhesive. Even after curing the adhesive, the assembly can be disassembled thermally, if necessary. Naturally, this and the other benefits and advantages combine to reduce costs.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, wherein like numerals indicate like elements, there are shown in the drawings simplified forms that may be employed, it being understood, however, that the invention is not limited by or to the precise arrangements and instrumentalities shown, but rather only by the issued claims. The drawings may not be to scale, and the aspects of the drawings may not be to scale relative to each other.

FIG. 2 is a block diagram illustrating an exemplary glass reference plate panel in accordance with one or more embodiments of the present invention.

FIG. 6 is a block diagram illustrating a system related to a glass reference plate assembly in accordance with one or more embodiments of the present invention.

DETAILED DESCRIPTION OF THE PRESENT INVENTION

Figure 1:
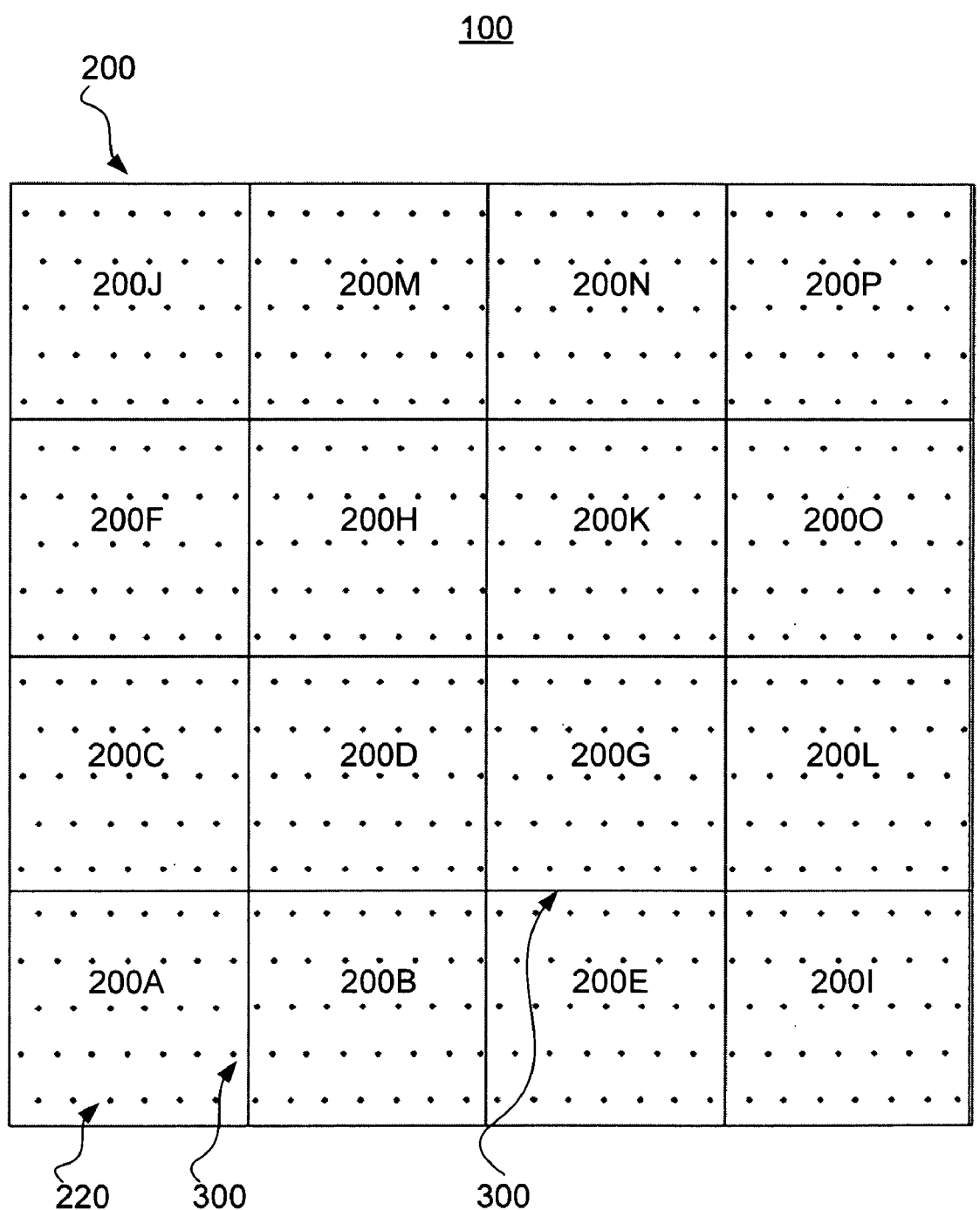
FIG. 1 is a block diagram illustrating an exemplary glass reference plate assembly in accordance with one or more embodiments of the present invention.

Referring to FIG. 1, a block diagram illustrates an exemplary glass reference plate assembly 100 in accordance with one or more embodiments of the present invention. The glass reference plate assembly 100 is a precision scribed glass master for use in an optical distortion measurement process. A glass reference plate, such as assembly 100, acts as an interface between a flat granite base of measuring gauge equipment and the product glass to be measured. By way of example, the product glass may comprise any glass, such as those used in flat panel display glass products (e.g., glass for LCD products). Examples of such glass include CORNING INCORPORATED GLASS COMPOSITION CODE 1737, CORNING INCORPORATED GLASS COMPOSITION NO. EAGLE$^{2000}$ ™, and CORNING INCORPORATED GLASS COMPOSITION NO. EAGLE XG™. These glass materials have numerous uses, in particular, for example, the production of liquid crystal displays (LCDs).

Glass reference plate assembly 100 includes multiple glass reference plate panels 200 arranged in an array. Upon being assembled, the panels 200 may be joined at lap joint interfaces 300 to form a substantially contiguous glass reference plate assembly. According to one or more embodiments of the present invention, the glass reference plate assembly 100 may be built using sixteen reference plate panels 200, such as panels 200A-200P depicted in FIG. 1, each approximately 810 mm$^2$ in size, arranged in a 4×4 array, and bonded together into a contiguous piece.

Referring to FIG. 2, a block diagram illustrates an exemplary glass reference plate panel 200 in accordance with one or more embodiments of the present invention. According to one or more embodiments of the present invention, the glass reference plate panels 200 are made using a glass having a CTE similar to that of the product glass to be measured. One or more embodiments of the glass reference plate may be constructed of Schott Borofloat Borosilicate Glass, ground and polished on both sides for a finished thickness of 6.8 mm.

The top side 202 of the plate 100 and panel 200 may be scribed for use as measurement witness marks, which are not shown. The nature and placement of the scribed measurement witness marks are dependent on the desired parameters of a given glass master configuration and within the knowledge and skill of a person of ordinary skill in the art. As the panels 200 are transparent, the witness marks may alternatively be scribed or otherwise formed on the bottom side 210. The bottom side 204 of the plate may have an opaque and/or reflective coating 210, such as a thin layer of aluminum, created, for instance, by physical vapor deposition (PVD) and protected by glass. Those skilled in the art will understand from the description herein that there are multiple options as to the material and deposition technique employed for the coating 210.

Each plate may be perforated with holes 220 to allow air flow as necessary to float (via positive air pressure of forced air) or hold (via negative air pressure of suction) the product glass as required. Due to the fragility and sensitivity of glass, such as to scratches, localized pressure on glass from hard surfaces may be advantageously avoided, so glass may be transported using distributed air pressure. For instance, product glass, or a panel 200, may be placed into location by lifting the product glass with vacuum grips into place. Positive air pressure through the plate assembly 100 may float the product glass to align and reposition it. Once in position, suction applied through the plate assembly 100 to the product glass may hold it in place relative to the plate assembly 100, so that consistent measurements may be made.

Although depicted as being rectangular in FIG. 1 and FIG. 2, the panels 200 may be any suitable geometry that allows the edges of adjoining panels 200 to abut to form a substantially continuous surface on the top side of plate assembly 100. For instance, triangles and hexagons would work also, but may increase the number of edges to prepare and interfaces to form. The top side surface is substantially continuous insofar as it accounts for surface variances such as holes 220, reference marks, reference edges 308, possible imperfections, etc.

Figure 3A:
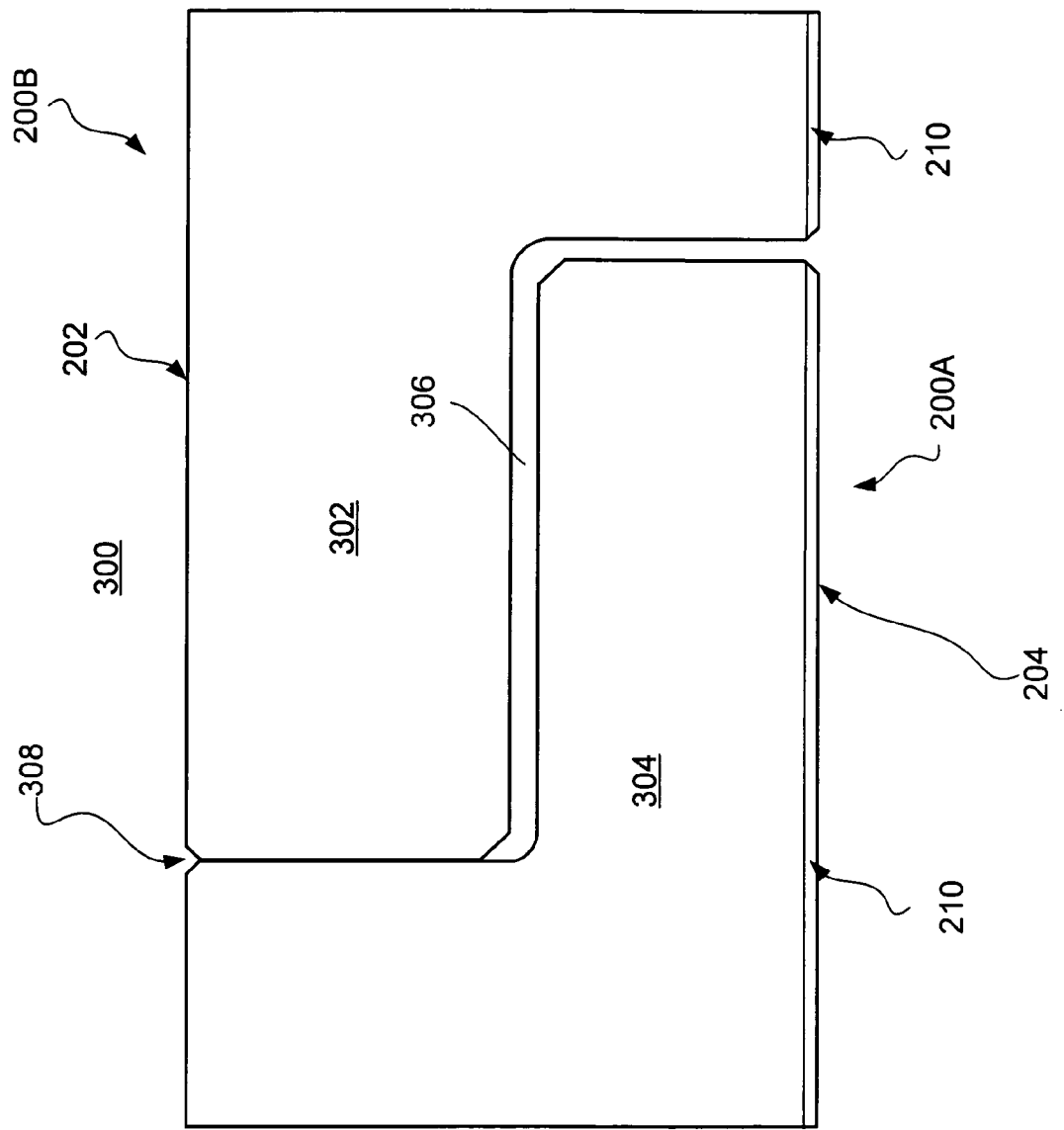
FIG. 3A is a block diagram illustrating an enlarged cross-sectional view of an exemplary lap joint interface of the exemplary glass reference plate assembly in accordance with one or more embodiments of the present invention.

Referring to FIG. 3A, a block diagram illustrates an enlarged cross-sectional view of an exemplary lap joint interface 300 of the exemplary glass reference plate assembly 100 in accordance with one or more embodiments of the present invention. According to one or more embodiments of the present invention, each glass reference plate panel 200 may include a lap joint connector 302, 304 on each adjoining edge to facilitate even and stable interfaces 300 with the edges of the adjoining plate panels 200. Connectors 302 and 304 combine to form means for connecting the adjoining panels 200. Edges that do not adjoin other panels 200 need not have a connector 302, 304.

Upper lap joint connector 302 extends from the upper side 202 of panel 200 on the right, e.g., panel 200B, and overlap lower lap joint connector 304, which extends from the bottom side 204 of panel 200 on the left, e.g., panel 200A. For instance, according to the placement of a panel 200, the panel 200 may be configured to have two upper lap joint connectors 302 along two edges and two lower lap joint connectors 304 along the other two edges. As between two adjacent panels 200, e.g., panels 200A and 200B in FIG. 3A, the panel 200 with the lower lap joint connector 304, e.g., panel 200A, may be considered the adhesive-carrier panel 200, inasmuch as the adhesive may be applied directly to the lower lap joint connector 304. Conversely, the panel 200 with the upper lap joint connector 302, e.g., panel 200B, may be considered the overlapping panel 200, inasmuch as the upper lap joint connector 302 overlaps the lower lap joint connector 304.

In the embodiment depicted in FIG. 3A, a gap 306 is created between connectors 302 and 304, and hence is defined by the means for connecting adjoining panels 200. The gap 306 provides space for application of an adhesive 307 (FIG. 3B) to bond panels 200A and 200B. Broadly speaking, the gap 306 refers to the absence of glass along the interface from two adjoining panels 200. The gap 306 is considered to exist irrespective of whether adhesive 307 has partially or completely filled the gap 306. The gap 306, however, may appear only on the bottom side 204 of the panels 200, so that the upper side 202 of each panel 200 of one or more embodiments abuts with each adjoining plate panel 200 via reference surfaces 308 on the edge plane ends of the individual plate panels 200.

A slight relief (e.g., a concavity) 309 (FIG. 3B) at or near a center of each panel 200 may be employed such that referencing contact is forced at the edges only of each adjoining panel 200. This reduces and/or eliminates the need for elevated levels of precision and subsequent expense of additional machining each panel 200 full length along the reference edges 308. Relief 309 also allows an area for adhesive displacement in the event that there is a slight excess of adhesive. This avoids the potential that excess adhesive would separate the reference surfaces, wit the resultant decrease in the overall alignment accuracy of the final assembly. Inasmuch as each plate panel 200 may be well fabricated as to thickness, further finishing may be avoided once the apparatus 100 is assembled.

The lap joint interface 300 between the panels 200 may be varied significantly and remain within the scope of the present invention. Building on the example of FIGS. 3A-B, a person of ordinary skill in the art would recognize from the description herein that the interconnection of the panels 200 may be accomplished by any number of connecting means, techniques and configurations, keeping in mind the goal of creating a substantially even, flat and contiguous surface of the plate assembly 100. Besides overlapping connectors 302, 304, variations might include tooth-and-groove configurations, frame arrangements, inter-panel braces, wire binding, etc.

Figure 3B:
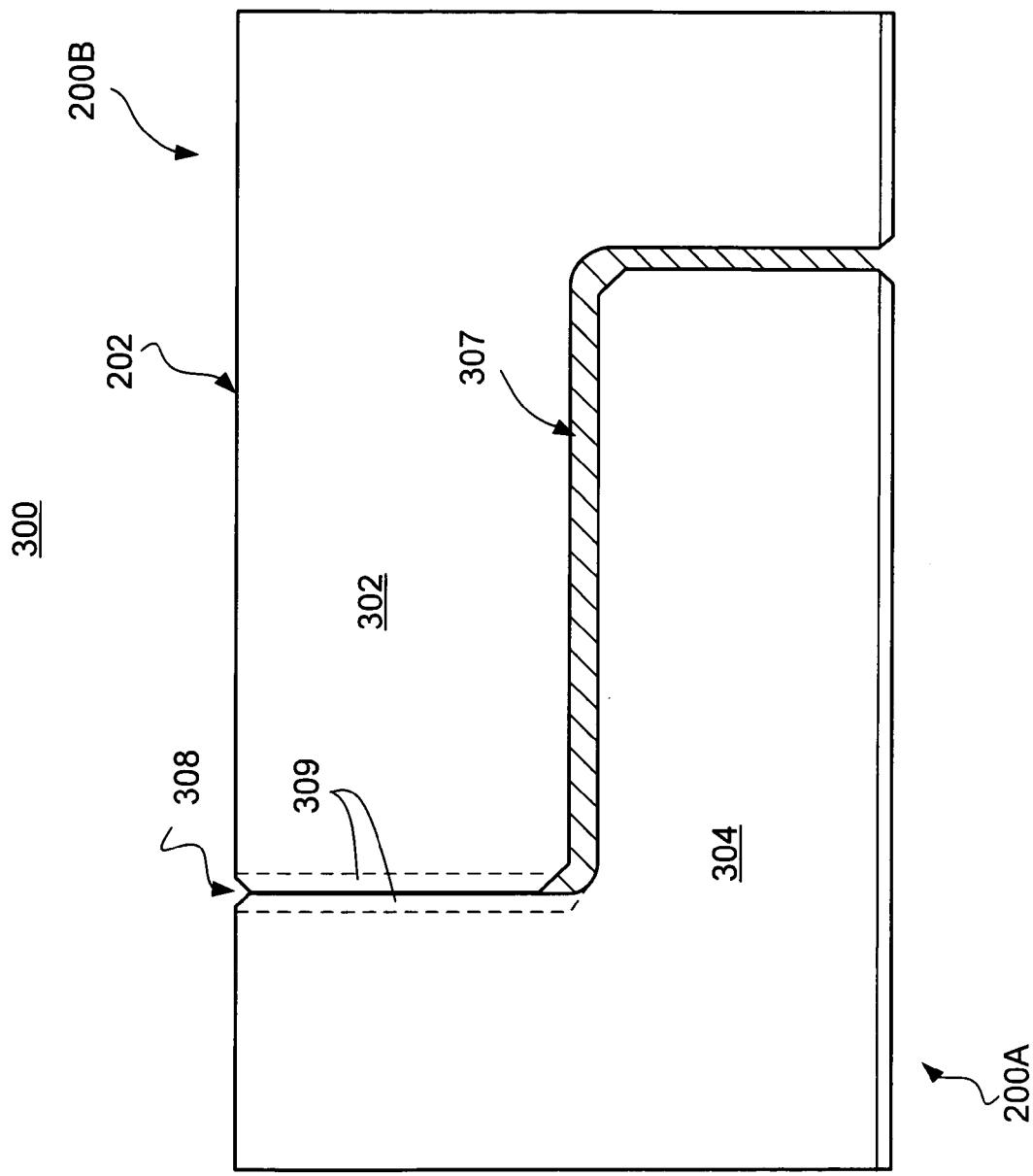
FIG. 3B illustrates the cross-sectional view of FIG. 3A in which adhesive has been added to the lap joint.
Figure 4C:
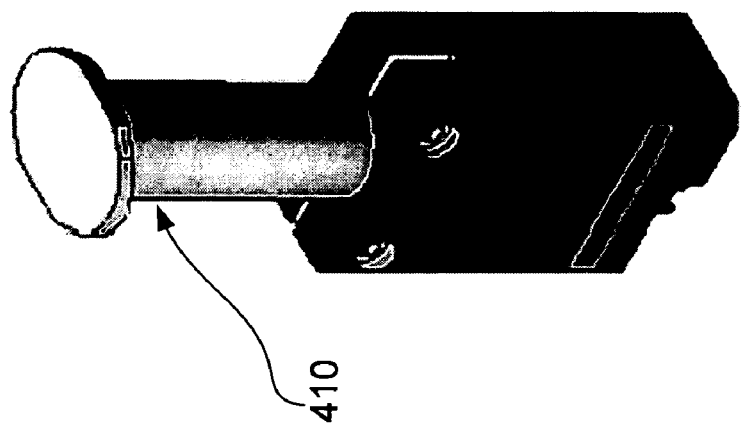
FIGS. 4A, 4B and 4C respectively are a side planar view, a cross-sectional view, and a perspective view of an exemplary adhesive applicator for use with the exemplary lap joint in accordance with one or more embodiments of the present invention.
Figure 4B:
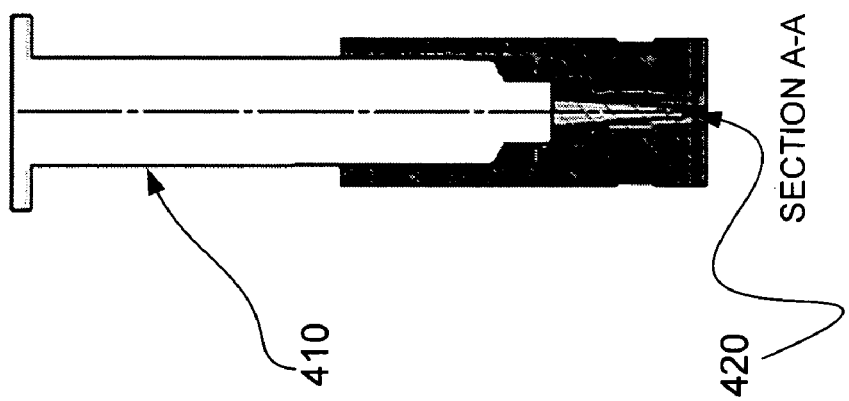
Figure 4A:
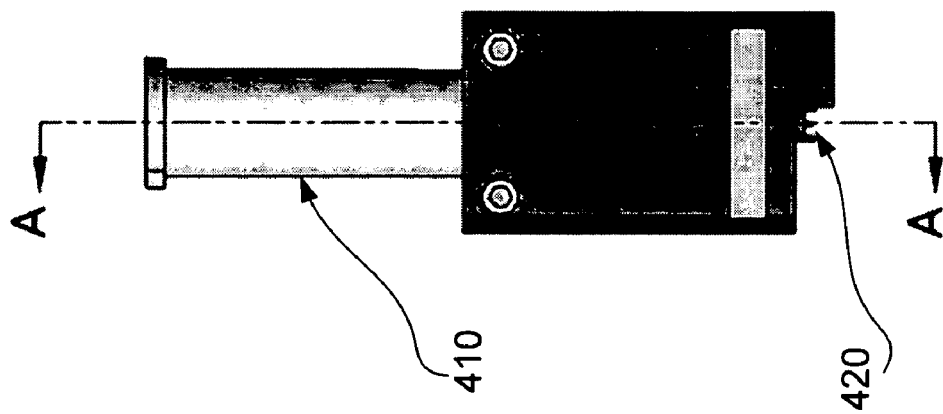

Referring to FIGS. 4A, 4B and 4C, each figure respectively shows one of a side planar view, a cross-sectional view, and a perspective view of an exemplary adhesive applicator 400 for use with the exemplary lap joint interface 300 in accordance with one or more embodiments of the present invention. The plate panels 200 may be bonded with an adhesive having properties matched to the glass, such as an ultraviolet (UV) light-curable adhesive. One or more embodiments may use a UV-curable adhesive coded BPA-3 from SPDV Polymer Labs. The UV-curable adhesive may be applied with a specially designed adhesive applicator 400 with a commercial dispensing system and cured with a UV lamp of appropriate wavelength emission (e.g., 350 nm). Adhesive applicator 400 may be designed specially to suit the interface 300 and/or match the means for connecting the adjoining panels 200. The adhesive applicator 400 may match the contour of the lower lap joint connector 304 so that an appropriate amount of adhesive 307 will distribute itself evenly within gap 306 (FIG. 3B). For ease of refilling the applicator 400, the adhesive may be dispensed from a removable and refillable syringe 410 having a needle tip 420 for controlled flow of adhesive.

Figure 5:
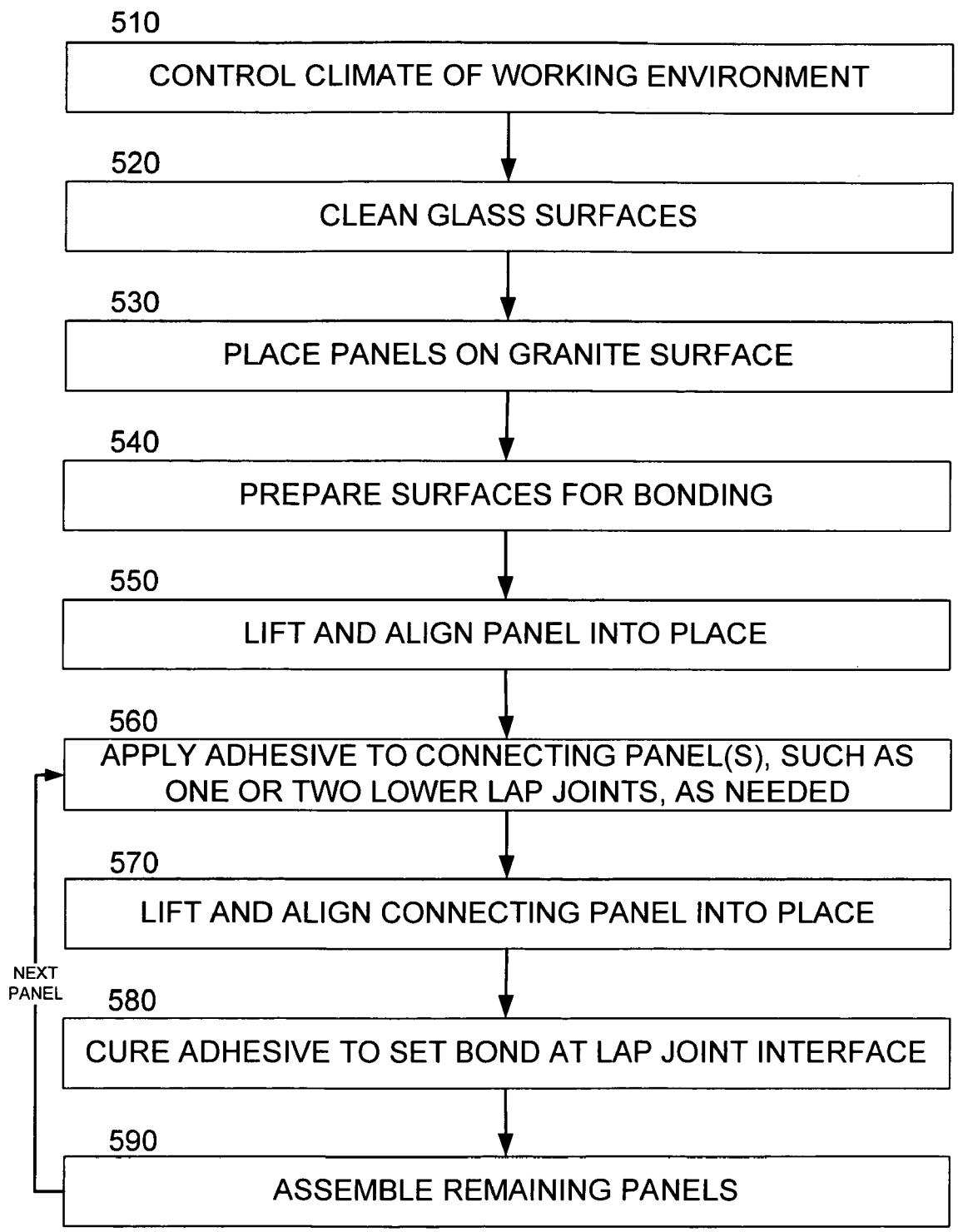
FIG. 5 is a flow diagram illustrating process actions that may be carried out to create a glass reference plate assembly in accordance with one or more embodiments of the present invention.

Referring to FIG. 5, a flow diagram illustrates process actions that may be carried out to create a glass reference plate assembly 100 in accordance with one or more embodiments of the present invention. An exemplary assembly process 500 may include some or all of the following actions.

In action 510 of process 500, environmental conditions may be controlled to provide a room temperature of 68 degrees F.+/−0.18 degrees F. (20 degrees C. +/−0.1 degree C.) and a room humidity of 45-50 RH+/−20%. In action 520, the entire surface of each glass panel 200 may be cleaned, such as using glass cleaning solution and a lint-free cloth. The holes 220 also may be cleaned and dried. In action 530, after cleaning the panels 200, the glass panels 200 may be placed on a granite surface of a distortion gauge system. In action 540, all surfaces to be bonded, their immediate areas and all corners may be prepared for bonding, such as washing in acetone using a lint-free cloth and lint-free cotton swabs. If necessary, isopropyl alcohol may be used next on bonding surfaces to drive off any moisture.

In action 550, starting with panel 200A, an adhesive-carrier panel 200 may be placed into location by lifting the adhesive-carrier panel 200 with vacuum grips into place and aligning the adhesive-carrier panel 200. In action 560, a controlled volume, such as a bead, of adhesive 307 (e.g., UV-curable adhesive) may be applied to a first lower lap joint connector 304, which will be used to form an adhesive bond at a horizontal interface at gap 306, e.g., beginning with the right edge of the adhesive-carrier panel 200A. In action 570, a first overlapping panel, e.g., panel 200B may be placed into location by lifting same with vacuum grips and aligning the panel 200B so as to adjoin it to adhesive-carrier panel 200A (see FIG. 3B). In action 580, the joint interface 300 between the adjoined adhesive-carrier and first overlapping panels 200A and 200B, may be cured by placing a cure lamp over the joint for 30 minutes.

In action 590, the remaining panels 200 may be assembled in alphabetical order, according to the configuration shown in FIG. 1. To assemble the remaining panels 200, actions 560, 570, and 580 may be repeated with respect to the second lower lap joint connector 304 on the second edge of the adhesive-carrier panel 200, e.g., the top edge of panel 200A, to bond the second edge to a second overlapping panel 200, e.g., panel 200C. Having cured each joint interface of panel 200A, actions 560, 570 and 580 may be repeated for each remaining lower lap joint connector 304 on the remaining panels 200B-200P. With the curing of the interfaces 300 of panel 200P, the glass reference plate assembly 100 is assembled and in place.

Referring to FIG. 6, a block diagram illustrates a system 600 related to a glass reference plate assembly 100 in accordance with one or more embodiments of the present invention. System 600 is a system for the measurement of optical distortion of product glass. System 600 may include a glass reference plate assembly 100, a flat base 610, for example made of granite, and measuring gauge equipment 620. The glass reference plate assembly 100 rests on the flat granite base 610 and acts as an interface between the flat granite base 610 and the product glass 630 to be measured.

Before and after the product glass 630 to be measured is subjected to a glass shearing process by a glass shearing system 640, the product glass 630 is placed on the glass reference plate assembly 100, and measuring gauge equipment 620 notes the location of scribed reference marks on the product glass relative to scribed reference marks on a precision scribed glass master, here the glass reference plate assembly 100. By comparing the location of the scribed reference marks on the product glass relative to the scribed reference marks on the glass reference plate assembly 100 before and after the glass shearing process, a before-to-after change is measured, with which distortion introduced in the product glass during the glass shearing process can be determined.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of creating a modular glass reference plate assembly, the method comprising:
    providing a plurality of glass reference plate panels;
    arranging the plurality of glass reference plate panels into an array of adjoining glass reference plate panels with an interface therebetween and with a gap below a top side of the modular glass reference plate assembly within the interface; and
    adhering each of the glass reference plate panels to at least one adjoining glass reference plate panel along the interface.

2. The method of claim 1, further comprising: applying an adhesive to the interface and curing the adhesive with ultraviolet light.

3. The method of claim 2, wherein applying adhesive along the interface comprises using an adhesive applicator sized and shaped to match the interface.

4. The method of claim 1, wherein the step of adhering comprises abutting the glass reference plate panel and the adjoining glass reference plate panel along the interface to form a substantially continuous surface on a top side of the modular glass reference plate assembly.

5. The method of claim 1, further comprising forming a lap joint having a lower lap joint connector and an upper lap joint connector such that the upper lap joint connector overlaps the lower lap joint connector to form the interface and the gap.

6. The method of claim 5, wherein the step of adhering includes at least partially filling the gap with adhesive.

7. The method of claim 1, further comprising coating a bottom side of the plurality of glass reference plate panels with one or more of an opaque or reflective material or combinations thereof.

8. The method of claim 7, wherein the one or more of opaque or reflective material or combinations thereof comprises aluminum on the bottom side of the plurality of glass reference plate panels.

9. The method of claim 1, wherein:
    each glass reference plate panel is rectangular, and
    the array of adjoining glass reference plate panels comprises a rectangular arrangement four panels wide and four panels long.

10. The method of claim 1, wherein the plurality of glass reference plate panels comprises glass having a coefficient of thermal expansion similar to that of product glass to be placed on top of the modular glass reference plate assembly.

11. The method of claim 10, wherein the plurality of glass reference plate panels comprises borosilicate glass ground and polished on a top side and on a bottom side.

12. An apparatus, comprising:
    a substantially continuous top surface for receiving substrates; and
    a plurality of glass reference plate panels arranged in an array forming at least one interface between adjacent glass reference plate panels that are adhered to each other to form the top surface, the at least one interface includes a gap below the top surface in which an adhesive is disposed for the adhesion.

13. The apparatus of claim 12, wherein the adhesive is a UV-cured adhesive.

14. The apparatus of claim 12, wherein the interface includes a lap joint having a lower lap joint connector and an upper lap joint connector disposed such that the upper lap joint connector overlaps the lower lap joint connector to form the interface and the gap.

15. The apparatus of claim 12, wherein the plurality of glass reference plate panels includes holes for regulating air pressure above the top surface.

16. The apparatus of claim 15, wherein the regulation includes at least one of providing an air cushion for floating the substrate and vacuum for holding the substrate tight to the top surface.

17. The apparatus of claim 12, wherein one or more of the glass reference plate panels includes one or more of an opaque or reflective coating or combinations thereof on a bottom side thereof.

18. The apparatus of claim 17, wherein the one or more of opaque or reflective coating or combinations thereof comprises an aluminum coating.

19. The apparatus of claim 12, wherein:
    each glass reference plate panel is rectangular, and
    the array of adjoining glass reference plate panels comprises a rectangular arrangement of four panels wide and four panels long.

20. The apparatus of claim 12, wherein the plurality of glass reference plate panels comprises glass having a coefficient of thermal expansion similar to that of the substrate.

21. The apparatus of claim 12, wherein the plurality of glass reference plate panels comprises borosilicate glass ground and polished on at least a top side thereof.

22. The apparatus of claim 12, wherein one or more of the plurality of glass reference plate panels includes reference marks on at least one of a top side and a bottom side thereof.

23. A system for the measurement of optical distortion of product glass, the system comprising:
    a flat base;
    a modular glass reference plate assembly disposed on the flat base, and forming a substantially continuous top surface for receiving substrates, the top surface formed from a plurality of glass reference plate panels arranged in an array of adjoining glass reference plate panels adhered together along one or more interfaces, each interface includes a gap below the top surface in which an adhesive is disposed to facilitate the adhesion; and
    measurement gauge equipment operable to determine one or more characteristics of the substrates.

24. The system of claim 23, wherein the flat base comprises a flat granite base.

25. A modular glass reference plate panel for use in a modular glass reference plate assembly, the glass reference plate panel comprising means for connecting to at least one adjoining glass reference plate panel including a lap joint having a lower lap joint connector and an upper lap joint connector sized and shaped such that the upper lap joint connector of the glass reference plate panel overlaps a lower lap joint connector of the at least one adjoining glass reference plate panel to form an interface such that the glass reference plate panel and the at least one adjoining glass reference plate panel are connectable and adherable to form an array of adjoining glass reference plate panels adhered together.

26. The panel of claim 25, wherein the interface being operable to receive an adhesive for adhering the adjoining glass reference plate panel together.

27. The panel of claim 25, wherein the lower lap joint connector of the at least one adjoining glass reference plate panel and the upper lap joint connector of the glass reference plate panel define a gap below a top side of the modular glass reference plate assembly.

28. A method comprising:

measuring distortion in a flat product glass for display by using a distortion gauge wherein the distortion gauge comprises:
- a granite base;
- optical measurement equipment; and
- a precision scribed glass master on top of the granite base, wherein the precision scribed glass master has a continuous top surface made up of a plurality of glass reference plate panels arranged in an array such that each of the glass reference plate panels is adhered to at least one adjacent glass reference plate panel along an interface therebetween, wherein the interface includes a gap below the top surface in which an adhesive is disposed to facilitate the adhesion.

* * * * *

UNITED STATES PATENT AND TRADEMARK OFFICE
CERTIFICATE OF CORRECTION

PATENT NO. : 7,934,435 B2  
APPLICATION NO. : 11/634598  
DATED : May 3, 2011  
INVENTOR(S) : Douglas Edward Brackley et al.

It is certified that error appears in the above-identified patent and that said Letters Patent is hereby corrected as shown below:

*Col.*    *Line*

6    12        Please delete "20%" and add --2%--

Signed and Sealed this  
Nineteenth Day of July, 2011

David J. Kappos  
*Director of the United States Patent and Trademark Office*